United States Patent [19]

Adamich et al.

[11] Patent Number: 4,818,688
[45] Date of Patent: Apr. 4, 1989

[54] ASSAYS FOR ANTIBODY TO HEPATITIS B CORE ANTIGEN

[75] Inventors: Marina Adamich, Townsend, Del.; Susan M. Wos, Marlboro, Mass.

[73] Assignee: E. I. Du Pont de Nemours and Company, Wilmington, Del.

[21] Appl. No.: 933,617

[22] Filed: Nov. 21, 1986

[51] Int. Cl.$^4$ .................. G01N 53/00; G01N 33/543; C12P 21/00; C12N 15/00

[52] U.S. Cl. ...................... 435/7; 424/85.8; 424/86; 435/172.2; 435/240.27; 435/810; 435/948; 435/68; 436/518; 436/820

[58] Field of Search ............ 424/85, 86; 435/7, 172.2, 435/240.27, 810, 948, 68; 436/518, 820; 935/70, 107, 108, 110

[56] References Cited

U.S. PATENT DOCUMENTS

| | | | |
|---|---|---|---|
| 4,271,145 | 6/1986 | Wands et al. | 424/85 |
| 4,491,632 | 1/1985 | Wands et al. | 435/240.27 |

FOREIGN PATENT DOCUMENTS

| | | |
|---|---|---|
| 0013828 | 8/1980 | European Pat. Off. . |
| 0038642 | 10/1981 | European Pat. Off. . |
| 0003498 | 6/1986 | European Pat. Off. ............ 436/820 |

OTHER PUBLICATIONS

Hoofnagle et al, *The New England Journal of Medicine*, vol. 298, No. 25, pp. 1379–1383.
Chemical Abstract 103(19): 156873.
Siddle, N. *Alternative Immunoassays*, Chapter 3, pp. 13–36, (1985).
Tietz, *Clinical Guide to Laboratory Tests*, pp. 268–269, (1983).
Kohler and Milstein, *Nature*, vol. 256, pp. 495–497, Aug. 7, 1975.
Cianfriglia et al., *Hybridoma*, vol. 12(4), 451–457 (1983).
Tedder et al., *Journal of Hygiene*, Cambridge, vol. 90, 135–142, 1983.
Tedder et al., *Proceedings International Hepatitis Workshop*, 201–208, 1983.
Furuya et al., *Japan J. Med. Sci. Biol.*, 37 151–159 (1984).
Waters et al., *J. Med. Virology*, 19:79–86 (1986).
Tedder et al., *Journal of Medical Virology*, 6:323–332 (1980).

*Primary Examiner*—Robert J. Warden
*Assistant Examiner*—Carol A. Spiegel

[57] ABSTRACT

A single-antibody inhibition assay for detecting antibody to HBcAg using a labeled monoclonal antibody. A competitive ELISA method of screening hybridoma supernatants for monoclonal antibodies to HBcAg. A method of producing high affinity monoclonal antibody to rHBcAg by immunizing a mouse with rHRcAg using a short immunization schedule. Monoclonal antibodies to immunodominant epitope of HBcAg.

18 Claims, No Drawings

ASSAYS FOR ANTIBODY TO HEPATITIS B CORE ANTIGEN

TECHNICAL FIELD

This invention relates to an inhibition assay which utilizes a single monoclonal antibody to hepatitis B core antigen (HGcAg) to detect antibody to the antigen in human body fluid. It also relates to a method of producing monoclonal antibodies to HBcAg using recombinant HBcAg (rHBcAg) as immunogen and a short immunization schedule, and a competition assay method of screening hybridoma supernatants to detect monoclonal antibodies to HBcAg. The screening method can also be used to screen for antibodies to other immunogens. The invention also relates to certain monoclonal antibodies to HBcAg and hybridoma cell lines which produce them.

BACKGROUND ART

Infection with hepatitis B virus (HBV) is a worldwide public health problem, with chronic carriers accounting for approximately 10 percent of the population of Asia and Africa. Major causes of HBV-associated mortality are: chronic active hepatitis, liver cirrhosis and hepatocellular carcinoma. Both chronic carriers and newly infected individuals are at risk of succumbing to such complications. One important transmission route is the infection of newborn infants at parturition by mothers who have active infections or are chronic carriers. Other routes for transmission include contaminated blood or blood products used to treat other health problems.

On infection with HBV, large quantities of the virus and associated particles are present in the serum. These particles may contain DNA, but are largely empty viral envelopes which have hepatitis B surface antigen (HBsAg) on their surface. The appearance of antibodies to the HBsAg is usually not observed until approximately two months following the disappearance of circulating HBsAg. During this period, a person is highly infectious, but may be clinically diagnosed as non-infectious due to undetectable levels of HBsAg or antibodies to HBsAg. The viral particles present in the serum are known to shed their surface coat exposing the nucleocapsid. Both IgM and IgG class antibodies are produced to a protein of the nucleocapsid core. This protein is known as the hepatitis B core antigen (HBcAg). Early in infection, IgM anti-HBcAg antibodies are produced and their titres rise as circulating HBsAg titers fall. The titer of IgG anti-HBcAg antibodies increases as the titers of the IgM class antibodies fall and before the anti-HBsAg antibody titers rise significantly. It is therefore advantageous to test for the presence of IgM and IgG class antibodies to HBcAg in diagnosing HBV immune status.

Immunoassays have been developed for the detection of IgM anti-HBcAg antibodies and total anti-HBcAg antibodies. The commercially available assays for total anti-HBcAg antibodies are generally competitive assays using labeled human polyclonal antibody to HBcAg collected from infected donors to compete with unlabeled antibodies from the patient sample for binding to a solid phase coated with HBcAg. An example of a commercially available assay of this type is Corzyme TM Enzyme Immunoassay (Abbott Laboratories, Chicago, IL). The most common commercially available assays for IgM class antibodies can be called multilayer sandwich assays. A solid phase anti-IgM antibody is used to capture all IgM antibodies from a patient's sample. HBcAg is then added and binds to the specific IgM class anti-HBcAg from the same. Labeled human polyclonal anti-HBcAg is then used to detect any HBcAg bound to the support thus indicating the presence of IgM class anti-HBcAg in the sample. An example of a commercially available assay of this type is Corzyme TM M Enzyme Immunoassay (Abbott Laboratories). Both assays use large quantities of Human polyclonal anti-HBcAg. Other formats are possible.

The large amounts of human polyclonal anti-HBcAg antibodies needed for such assays must be collected, preferably from the same donor population each time, isolated, purified and labeled with a radioisotope or enzyme. There is significant health hazard and expense associated with this extensive processing of contaminated blood. It would be advantageous to obtain a constant and consistent supply of antibody to HBcAg without exposure to such a health risk. This need can be met by a monoclonal antibody which can substitute in these immunoassays.

Kohler and Milstein first reported the estabilshment of a continuous hybrid cell line secreting a monoclonal antibody in 1975 [Nature, Volume 256, 495 (1975)]. Since then the process for producing monoclonal antibodies to a variety of antigens has become well known in the art. The production of monoclonal antibodies with specific desirable properties to any given antigen cannot be predicted from the teachings of the art.

Cianfriglia et al. [Hybridoma, Vol. 12(4), 451–457 (1983)] disclose a short-term immunization schedule for producing hybridomas secreting antibodies.

Monoclonal antibodies for HBsAg have been disclosed by many groups (e.g., Wands et al., U.S. Pat. No. 4,271,145 issued June 2, 1981, and U.S. Pat. No. 4,491,632 issued Jan. 1, 1985). Wands et al. report it is critical that the first administration of antigen be given intraperitoneally and second administration be given intravenously at least 3 week later. The antigen used for immunization was isolated from contaminated human plasma. Cell fusion was done by known techniques. Three tests were used to assess anti-HBsAg activity. Binding of antibody to HBsAg coated microtiter plates was probed with either [$^{125}$I]-HBsAg or [$^{125}$I]-goat anti-mouse F(ab')$_2$. The third assay tested the ability of the anti-HBsAg to aggutinate human O-negative red blood cells coated with HBsAg. They suggest that such a process would also be useful for producing monoclonal antibodies to HBcAg.

Tedder et al. [Journal of Hygiene Cambridge, Volume 90, 135–142 (1983) and Proceedings International Hepatitis Workshop, 201–208 (1983)]report the production of six monoclonal antibodies for HBcAg. Mice were immunized with 3 to 4 successive intraperitoneal injections of 50 to 100 µg of HBcAg purified from infected liver. Clones secreting anti-HBcAg were identified using a capture assay comprising: binding all available mouse IgG to a solid phase coated with rabbit anti-mouse IgG, adding purified HBcAg to bind to any anti-HBcAg present, adding [$^{125}$I]-human anti-HBcAg and determining how much radioactivity bound to the support. The presence of radioactivity bound to the support indicated the clone tested was secreting anti-HBcAg. Tedder et al. also state that an alternative assay for detection of anti-HBcAg-secreting hybrids might have been one of the commercially available competitive RIA or ELISA tests. They state however that such an assay would be expected to be of limited value since the monoclonal antibody will block only a single epitope of those present on the solid phase HBcAg. Tedder et al. report testing supernatants from the 6 hybridomas secreting monoclonal anti-HBcAg antibodies using a competitive RIA, but state that the level of inhibition obtained (ranging from 32 to 88%) would not have permitted reliable detection of the antibodies by the competitive RIA alone.

Tedder et al. disclose using the monoclonal anti-HBcAg antibodies in a liver biopsy for presence of HBcAg. They do not disclose use of the antibodies in an inhibition (e.g. competition) assay to detect antibodies to HBcAg in body fluid.

Furuya et al. [Japan J. Med. Sci. Biol., 37, 151–159 (1984)] also report production of monoclonal antibodies to HBcAg. Mice were immunized with HBcAg purified from human plasma by subcutaneous and intramuscular injections 3 times at one-week intervals. Clones secreting anti-HBcAg were identified by immune adherence hemagglutination (IAHA) and reverse passive hemagglutination (RPHI) techniques. The number of monoclonal antibodies detected by both tests was 18. Furuya et al. do not teach use of a competitive assay for detection of monoclonal antibodies to HBcAg in hybridoma supernatants.

Furuya et al. disclose labeling the monoclonal antibodies with peroxidase and utilizing them in an inhibition assay to determine anti-HBcAg antibodies in serum. Serum containing anti-HBcAg antibodies was incubated with an optimal dose of HBcAg. Glass beads coated with anti-HBcAg monoclonal antibody were added, followed by peroxidase labeled anti-HBcAg monoclonal antibody then o-phenylenediamine. The enzyme reaction was stopped and absorbance (optical density, O.D.) was measured. Percent inhibition was calculated as follows:

$$\text{Inhibition \%} = \frac{\text{Negative Control (O.D.)} - \text{Sample (O.D.)}}{\text{Negative Control (O.D.)} - \text{Positive Control (O.D.)}} \times 100$$

The Furuya et al. assay is a double antibody assay. The immobilized and labeled monoclonal antibodies must bind to different sites on the HBcAg molecule. If they bound to the same site a false positive would result because the binding site would be occupied by the immobilized antibody and the labeled antibody could not bind. This means the immobilized and labeled antibodies must either be different and specific for different epitopes on the HBcAg molecule, or they must be specific for an epitope which occurs more than once on the HBcAg molecule. Perhaps because of these limitations, it is believed that assays for anti-HBcAg of the double monoclonal antibody type have not been commercialized.

In both Tedder et al. and Furuya et al. the anti-HBcAg monoclonal antibodies were produced by immunization of mice with human HBcAg. The purification of HBcAg from human liver or plasma is laborious and constitutes a significant health hazard. Murray et al. (EP 0,013,828 published Aug. 6, 1980) disclose an *E. coli* transformed with recombinant DNA coding for HBcAg. The polypeptide expressed by this transformed *E. coli* reacts with human polyclonal anti-HBcAg antibodies and is referred to as rHBcAg.

SUMMARY OF THE INVENTION

This invention provides an improved single-antibody inhibition assay for detecting antibody to HBcAg in a patient sample by:

(1) incubating the sample and labeled antibody to HBcAg with HBcAg bound to a solid support;

(2) washing the support to remove unbound labeled antibody; and (3) measuring the signal generated by labeled antibody bound to the HBcAg or not bound to the HBcAg.

The improvement comprises using as the labeled antibody a monoclonal antibody which competes effectively with human anti-HBcAg polyclonal antibody in a competitive ELISA assay.

In the assay of this invention the sample and labeled monoclonal antibody can be incubated with the bound HBcAg simultaneously, or the sample can be incubated first. Both procedures are referred to as inhibition assays. The procedure involving simultaneous incubation is also referred to as a competitive assay. The antibody can be labeled by direct attachment of a detectable moiety or through association with another substance that binds to the antibody and is itself directly attached to the detectable moiety.

This invention includes a reagent kit for conducting the improved assay comprising HBcAg bound to a support and a labeled monoclonal antibody.

The invention also includes a competitive immunoassay method of screening hybridoma supernatants for monoclonal antibodies to HBcAg which are useful in the assay of this invention. This screening method comprises:

(1) incubating supernatant samples and labeled human anti-HBcAg polyclonal antibodies with HBcAg bound to a support;

(2) washing the support to remove unbound labeled antibodies; and (3) detecting the bound labeled antibodies.

The screening method of this invention has general applicability for detecting antibodies to antigens having multiple epitopes. By using labeled human polyclonal antibodies to the antigen, monoclonal antibodies capable of competing effectively with polyclonal antibodies can be identified.

The invention also includes a method of producing a high affinity monoclonal antibody to rHBcAg which comprises immunizing a mouse with intraperitoneal and intravenous injections of rHBcAg totalling less than 100 μg over a period less than 3 weeks, fusing spleen cells from the immunized mouse with mouse myeloma cells, culturing the fused cells in selective medium to produce a continuous hybrid cell line and cloning the cells to isolate those producing the desired antibody. Finally, the invention includes certain cell lines and monoclonal antibodies produced by this method.

Prior to this invention it was not predictable that a labeled monoclonal antibody to HBcAg could be produced which would have practical utility in a single-antibody inhibition assay in place of labeled human polyclonal anti-HBcAg. HBcAg, a large protein, would be expected to have multiple epitopes, and a given epitope could produce an immune response in some persons but not others. A monoclonal antibody to that epitope could produce a false negative in a person having no immune response to that epitope.

In connection with this invention, it has been found that a labeled monoclonal antibody to HBcAg can be used in a single-antibody inhibition assay, provided the antibody is one which competes effectively with human polyclonal anti-HBcAg. It is considered that a monoclonal anti-HBcAg antibody competes effectively if it produces at least 40% competition in the competitive ELISA assays described in Example 1(c)(i)(a) and (b) below, where % competition is calculated as $$\frac{\text{Negative Control Response} - \text{Sample Response}}{\text{Negative Sample Response}} \times 100$$

where Response is optical density, absorbance or fluorescence.

The results obtained in this invention indicate that an immunodominant epitope or site on HBcAg exists and that the monoclonal antibodies produced as described herein are specific for that epitope or site. A site, as the term is used herein, consists of closely related or adjacent epitopes. An immunodominant epitope or site is an epitope or site which is recognized by polyclonal antibodies produced by substantially all host organisms. This means that at least a portion of the antibodies which comprise the total polyclonal population of each host must recognize this epitope or site.

DESCRIPTION OF THE INVENTION

Production of the monoclonal antibodies of this invention begins with the immunization of a mouse. Female BALB/c mice are preferred, however, other strains of mice are expected to function. The immunogen used can be a crude, semi-purified or purified preparation of HBcAg. It is preferred that a recombinant HBcAg is used and the recombinant HBcAg produced in *E. coli* by Green Cross Co. of Japan is most preferred.

Surprisingly, it has been found that very short immunization protocols are effective in stimulating production of high affinity monoclonal antibodies. The most preferred immunization schedule is set forth in Example 1. Other short term schedules are expected to be effective. These schedules should generally include administration of less than 100 μg of immunogen, and preferably about 50 μg over a period of less than 3 weeks, and preferably 2 weeks. The immunogen used can be mixed with an adjuvant such as Freund's complete or incomplete adjuvant. While it is preferred that the immunization be done in vivo as described above in vitro procedures are known and expected to function.

A variety of procedures are known in the art for fusing the spleen cells of an immunized animal with a myeloma cell line to produce a continuous hybrid cell line. Any of these procedures are expected to function, but the method of Kohler and Milstein [European Journal of Immunology, Volume 6, 511–519 (1976)] is preferred. The spleen cells subjected to this fusion procedure may be the entire population of cells present or a subset of these cells that have been selected on the basis of having surface immunoglobulin reactive to the antigen of interest. The ratio of spleen cells to myeloma cells can range from about 1:1 to about 10:1, however, the preferred ratio is about 5:1. A total volume of about 0.5 to 1.0 mL of fusion medium is appropriate for $10^8$ spleen cells.

Many myeloma cell lines are known and generally available. Any of these can be used. The cell line chosen should have a selectable marker, such as a drug susceptibility, so that unfused myeloma cells will not survive in a selective medium, while the hybrids will survive. It is also preferred that the cell line is a "non-secretor", that is, it does not produce an endogenous immunoglobulin prior to fusion. While not preferred, "secretor" cell lines can be used. The preferred fusion promoter is polyethylene glycol (PEG) having a molecular weight of about 1,000 to 4,000. Other fusion promoters or electrofusion techniques are expected to function.

Following fusion the mixture of fused cells, unfused spleen cells and unfused myeloma cells are diluted and cultured in a selective medium which will not support growth of the unfused myeloma cells. The selective medium most commonly used is HAT (hypoxanthine, aminopterin and thymidine) medium. After about 1 week in this medium unfused myeloma and unfused spleen cells die. The cells can be subjected to limiting dilution so as to result in the placing of 1 cell in each tissue culture container.

The supernatant in each cell culture container is evaluated for the presence of antibody specific for HBcAg. A variety of assay configurations can be used to identify antibodies which react with HBcAg, but in order to select a monoclonal antibody which competes effectively with human polyclonal antibody, it is preferred to conduct a competitive immunoassay screening method using human polyclonal antibodies specific for HBcAg. These human anti-HBcAg antibodies are isolated from infected individuals. One suitable assay is described below, variations will be readily apparent to one of ordinary skill in the art. The assay is conducted by adsorbing a small amount, typically about 50 ng, of HBcAg to a suitable solid support, typically a microtiter plate. The supernatant from a cell culture container is then allowed to compete with labeled human polyclonal anti-HBcAg antibodies. Human anti-HBcAg conjugated to HRP (horseradish peroxidase) from Abbott Laboratories is the preferred labeled anti-HBcAg. Following a suitable incubation period, the solid support is washed and the amount of label bound is determined. Hybridomas secreting antibody which substantially inhibits the binding of the human polyclonal anti-HBcAg are selected for further characterization. The use of low concentrations of HBcAg on the support and the use of short incubation times, generally less than about 1 hour, promote the selection of high affinity antibodies.

By use of the above methods, five hybridomas have been identified which secrete monoclonal antibodies which compete effectively with human antiHBcAg. These antibodies and corresponding cell lines are designated 7A6.4; 7A7; 7A13.1: 7A14.1 and 7A15.1. The cell lines have been deposited in the American Type Culture Collection (ATCC), Rockville, MD., in accordance with MPEP 608.01 p. ATCC accession numbers are HB-9262, HB-9264, HB-9263, and HB-9261, respectively. The first three antibodies are IgG2b subclass and the last two are IgG1 subclass.

While the selection of a monoclonal antibody specific for an immunodominant epitope or site of HBcAg has been described, this method is expected to be generally applicable to other antigens in other systems. This should be useful in identifying an immunodominant epitope or site on other human viral antigens or animal antigens of interest.

If a recombinant antigen is used for immunization, it should be demonstrated that the chosen antibody does not react with other antigens present in the expression system. It should also be shown that the antibody reacts comparably with both natural and recombinant antigen. This is particularly important if the antibody is intended for use in an assay method with the recombinant antigen. These assays can be conducted by the well-known ELISA procedures. In the present case, the hybridomas selected were shown not to react with any components of an *E. coli* lysate and also to react comparably to natural HBcAg and recombinant HBcAg. Since the hepatitis B e antigen (HBeAg) is known to be related to the HBcAg it is desirable to determine if the chosen antibodies react with HBeAg antigens. The class and subclass of the monoclonal antibodies are determined by known procedures.

The selected hybrid cell lines are further cloned by limiting dilution to ensure that the cell population is derived from one cell clone and that the hybridoma is stable and producing the desired antibody. Once completed, small amounts of the cells and antibodies can be produced by culturing in a suitable medium for a time. Procedures for accomplishing such culturing are well known.

In order to produce larger amounts of antibodies, the desired hybridoma is injected into the peritoneal cavity of mice where the cells reproduce and secrete the antibody into the ascites or peritoneal exudate. This is accomplished by growing the hybrid cell line in tissue culture flasks until about $1 \times 10^7$ cells are available for injection into a mouse. Prior to injection into BALB/c mice the mice are primed with 2,6,10,14-tetramethylpentadecane. Two to three weeks after injection of the hybridoma cells ascites is collected. The ascites is centrifuged at $1000 \times g$ at $4°$ C. for 15-minutes to produce an ascitic supernatant containing the desired antibody. The fact that the desired antibody is obtained is confirmed by subjecting the antibody from the ascites to the same series of assays used initially to select and characterize the antibody obtained from tissue culture.

The monoclonal antibody from the ascites can be further purified as desired. This can be accomplished by a variety of known methods.

The monoclonal antibodies of this invention can be conjugated to different enzymes using a variety of known procedures. It is generally preferred to use horseradish peroxidase (HRP) or alkaline phosphatase (ALKP). These monoclonal antibodies can also be labeled with other types of labels such as fluorescent labels, radioisotopes or others.

Labeled monoclonal anti-HBcAg antibodies are useful in conducting competitive assays for detecting immunoglubulins displaying anti-HBcAg specificity. Labeling of these antibodies can be accomplished in many ways including direct attachment of a detectable moiety or by association with another substance which binds to the antibody and is itself directly attached to a detectable moiety. Suitable detectable moieties include enzymes, fluorescent probes, and isotopes. Other substances which can bind to antibodies and can be labeled themselves include Protein A and anti-species specific antibodies (e.g., anti-mouse IgG antibody). The typical format for such an assay is to supply a solid phase coated with HBcAg and allow the antibodies suspected of being in a patient sample to compete with a labeled antibody for binding to HBcAg. If the sample contains anti-HBcAg antibodies, these antibodies will inhibit the binding of the labeled antibodies. If an enzyme is used as the label, the result will be a low absorbance when the presence of enzyme is determined by adding a substrate for the enzyme. If the sample does not contain anti-HBcAg antibodies then the labeled antibodies will bind to the HBcAg and a high absorbance will result.

If the labeled monoclonal antibodies of this invention are to be useful in such as assay, they must compete effectively against substantially all human polyclonal anti-HBcAg antibody samples. Another way of viewing this is, if substantially all human polyclonal anti-HBcAg antibody samples do not contain a population of antibodies which recognize the same epitope as the monoclonal antibodies then the monoclonals will not be clinically useful. That is because those human polyclonal anti-HBcAg antibody samples not recognizing the epitope recognized by the monoclonal antibody will be miclassified as not containing anti-HBcAg antibodies, possibly leading to misdiagnosis of the clinical state of the patient. If an epitope is recognized by substantially all human polyclonal anti-HBcAg antibody samples then that site can be said to be immunodominant.

That monoclonal antibodies of this invention are specific for an immunodominant epitope of HBcAg has been demonstrated as follows. Monoclonal antibodies 7A6.4 and 7A13.1 were conjugated to HRP using the periodate method described below then diluted 1:2000 and 1:2400. 50 ng rHBcAg from Green Cross (Japan) was coated onto individual wells of a microtiter plate. Equal volumes of HRP conjugated monoclonal antibody and patient plasma were added to each well and incubated at room temperature for 90 minutes. The plate was then washed and the substrate o-phenylenediamine (OPD) was added to each well and incubated at room temperature for 15 minutes. The enzymatic reaction was halted by addition of 1 N sulfuric acid and the absorbance at 492 nm determined. 21 patient samples were classified as positive based upon clinical presentation and/or independent evaluation of hepatitis markers. The polyclonal anti-HBcAg antibodies present in all 21 samples competed effectively with the HRP labeled 7A6.4. 48 negative samples were also tested and found not to contain antibodies which competed with HRP labeled 7A6.4.

A data set from one experiment comparing results with 7A6.4, 7A13.1 and the commercial Corzyme ™ assay (Abbott Laboratories) is presented in Table 1 below.

TABLE 1

| | PATIENT RESULTS | | | | | |
|---|---|---|---|---|---|---|
| | HRP-7A6.4 | | HRP-7A13.1 | | CORZYME ™ | |
| Patient # | Abs. 492 nm | Result | Abs. 492 nm | Result | Abs. 492 nm | Result |
| Pos. Control | 0.002 | + | 0.004 | + | 0.021 | + |
| 1 | 0.135 | + | 0.356 | + | 0.027 | + |
| 2 | 0.014 | + | 0.020 | + | 0.023 | + |
| 3 | 1.112 | − | 1.276 | − | 0.871 | − |
| 4 | 1.137 | − | 1.263 | − | 1.023 | − |
| 5 | 1.174 | − | 1.143 | − | 0.812 | − |
| 6 | 0.245 | + | 0.403 | + | 0.036 | + |
| 7 | 1.065 | − | 1.275 | − | 0.417 | + |
| 8 | 0.110 | + | 0.414 | + | 0.049 | + |
| 9 | 0.944 | − | 1.332 | − | 0.991 | − |
| 10 | 0.910 | − | 1.321 | − | 0.888 | − |
| Neg. Control | 1.223 | − | 1.119 | − | 1.108 | − |

These results indicate that monoclonal antibodies 7A6.4 and 7A13.1 of this invention recognize an immunodominant epitope and that the methods of this invention provide clinically useful results equivalent to a commercial method based upon human polyclonal antibodies.

EXAMPLE 1

PRODUCTION OF MONOCLONAL ANTIBODIES TO HEPATITIS B CORE ANTIGEN

A. Immunization and Fusion

Female BALB/c mice were immunized with recombinant hepatitis B core antigen (rHBcAg) that was expressed in an *E. coli* vector system (Green Cross Corp., Osaka, Japan). The mice received 5 injections totaling 50 μg over a two-week period. The first injection consisted of 10 μg emulsified in Freund's complete adjuvant and was given intraperitoneally. This injection was repeated on day 7. The mice then received on 3 consecutive days injections without adjuvant consisting of 10 μg intraperitoneally on day 13, 5 μg intraperitoneally and 5 μg intravenously on day 14 and 5 μg intraperitoneally and 5 μg intravenously on day 15. Two days later a mouse was sacrificed and the spleen removed.

Single cell suspensions of spleen cells and murine myeloma P3-X63/Ag8.653 cells were prepared by standard methods. $1 \times 10^8$ spleen cells were combined with $2.7 \times 10^7$ P3-X63/Ag8.653 myeloma cells and the cells pelleted by low speed centrifugation. The media was aspirated and the pellet dislodged by gently tapping. The polyethylene glycol (PEG) solution (0.8 mL), comprised of 45% PEG (with an average molecular weight of 1500) and 5% dimethylsulfoxide in Iscoves medium (Irvine Scientific, Santa Anna, CA), was added dropwise over a period of 1 minute followed by a 1 minute incubation in a 37° C. water bath. Twenty milliliters of Iscoves medium supplemented with 10% fetal calf serum, 0.1 mM hypoxanthine, and $1.6 \times 10^{-5}$M thymidine was added and the cells plated into twelve 96-well plates containing feeder layer comprised of mouse peritoneal macrophages.

B. Selection and Growth of Hybridoma

After cells were fused, they were cultured in Iscoves medium supplemented with 10% fetal calf serum, 0.1 mM hypoxanthine, $4.0 \times 10^7$M aminopterin, and $1.6 \times 10^{-5}$M thymidine (HAT medium) at 37° C. with 5% $CO_2$ in a humid atmosphere. Several weeks later, when visible clones were present in 301 of the wells, the tissue culture supernatants were tested for antibody secretion. Monoclonal antibodies to HBcAg were identified by reactivity in a competitive ELISA using rHBcAg coated plates as described in C below. Antibodies to *E. coli* proteins were detected by an indirect ELISA on plates coated with *E. coli* lysate, also described in C below.

C. Characterization of Monoclonal Antibody Reactivity (i) Competitive ELISA (a) Tissue culture supernatants were tested for antibody activity to rHBcAg in a competitive assay with horseradish peroxidase (HRP) conjugated human polyclonal antibody to HBcAg (HRP-human anti-HBcAg, from a Corzyme ™ Enzyme Immunoassay Kit, Abbott Laboratories, Chicago, IL, minimum concentration 2 μg/mL). Polystyrene microtiter plates (Immulon II, Dynatech, Alexandria, VA) were coated with 100 μL containing 50 ng of rHBcAg protein diluted in 0.05M carbonate-bicarbonate buffer, pH 9.6. After overnight adsorption at 4° C., the wells were washed three times with phosphate-buffered saline (PBS), pH 7.2 containing 0.1% bovine serum albumin (BSA). Non-reacted sites on the polystyrene were blocked with 1% BSA-PBS for 1 hour at ambient temperature. The solution was aspirated and 100 μL of premixed tissue culture supernatant and HRP-human anti-HBcAg (1:1) was added to the wells. After a 1-hour incubation at room temperature and another cycle of plate washing, 100 μL of substrate, 0.4 mM 2,2'-azno-di(3-ethyl-benzthiazoline sulfonate) in 0.05 M Citric Acid pH 4.0 containing 0.3% $H_2O_2$ (ABTS, Kirkegaard and Perry, Gaithersburg, MD), was added to each well. The plates were incubated for 20 minutes at room temperature, followed by measuring the absorbance at 410 nm in a microtiter plate reader. Seven hydridomas secreting antibody which inhibited binding of the human polyclonal antiserum to rHBcAg by more than about 40%, calculated versus negative human serum control were selected for further evaluation.

(b) Tissue culture supernatants from the seven hybridomas producing monoclonal antibodies reactive to recombinant HBcAg were tested using the Corzyme ™ Enzyme Immunoassay Kit and following the procedure described in Abbott's product insert. Supernatants were mixed (1:1) with HRP-human antiHBcAg (minimum concentration 2 μg/mL) and 300 μL of the mixture was incubated with one polystyrene bead coated with HBcAg derived from plasma of humans infected with Hepatitis B virus. Following a 2-hour incubation at 40° C. in a water bath, the liquid was aspirated and the bead washed 3 times with 4 to 6 mL distilled water. The beads were transferred into assay tubes and 300 μL of 23.7 mM OPD solution [o-phenylenediamine-2 (HCl)] in citrate-phosphate buffer containing 0.002% hydrogen peroxide was added and allowed to react for 30 minutes at room temperature. The reaction was stopped with 1 mL of 1N sulfuric acid and the absorbance determined at 492 nm. The seven cell lines all produced monoclonal antibodies that reacted with the human derived HBcAg and inhibited binding of the human polyclonal antibodies to the HBcAg by more than about 40%, calculated versus negative human serum control. The cell lines were also tested for presence of antibodies to *E. coli* proteins as described next.

(ii) Indirect ELISA.

Immulon II plates were coated with 50 μL containing 50 ng of recombinant HBcAg or 5 μg sonicated *E. coli* as described above. The plates were blocked with 1% BSA-PBS and 50 μL of tissue culture supernatant was added to the wells. Plates were incubated for 1 hour at 37° C., washed three times with 300 μL of 0.1% BSA-PBS followed by adding 50 μL of HRP-goat anti-mouse immunoglobulins (Cooper Biomedical, Malvern, PA), diluted 1:2,000 in 0.1% BSA-PBS, into each well. After a 1-hour incubation at 37° C., the plates were washed as described previously, and color developed using substrate solution containing ABTS. Absorbance measurement at 410 nm indicated all 7 cell lines were positive for anti-HBcAg but negative for anti-*E. coli* proteins.

Following the indirect ELISA test the 7 cell lines were expanded, re-cloned by limiting dilution and retested sevberal times in the competitive ELISA assay described in C(i)(b) above using in some tests rHBcAg and in other tests human-derived HBcAg. They were also tested for Ig subclass and cross-reactivity. When retested, 5 to of the 7 re-cloned cell lines were found positive for monoclonal antibodies to HBcAg.

(iii) Subclassing of the monoclonal antibodies was done using recombinant HBcAg coated plates as described above. Specific subclassing conjugates were purchased from Zymed Laboratories (So. San Francisco, CA) and were used at a 1:300 dilution in 0.1% BSA-PBS.

(iv) Cross-reactivity Assays

The specificity of the monoclonal antibodies to HBcAg versus other hepatitis B virus antigens was determined by testing for cross-reactivity to hepatitis e antigen and surface antigen using commercially available assays (Anti-HBe EIA and AUSRIA, Abbott Laboratories) and following vendor's instructions.

Characterization of the antibodies is shown in Table 2. Average results from the repetitions of the ELISA competitive assays C(i)(b) are presented in Table 3.

TABLE 2
CHARACTERISTICS OF MONOCLONAL ANTIBODIES TO HBcAg

| Monoclonal Antibody | Subclass | Specificity* | | | |
|---|---|---|---|---|---|
| | | E. coli | HBsAg | HBcAg | HBeAg |
| 7A6.4 | IgG$_{2b}$ | − | − | + | − |
| 7A7 | IgG$_{2b}$ | − | − | + | − |
| 7A13.1 | IgG$_{2b}$ | − | − | + | − |
| 7A14.1 | IgG$_1$ | − | − | + | − |
| 7A15.1 | IgG$_1$ | − | − | + | − |

*Reactivity to E. coli proteins or hepatitis B virus antigens as determined by immunoassays. No reactivity denoted by a negative sign (−) while reactivity is denoted by a positive sign (+).

TABLE 3

| Competing Monoclonal Antibody | % Competition* | |
|---|---|---|
| | Recombinant HBcAg | Human-derived HBcAg |
| 7A6.4 | 96.7 ± 1.1 | 87.7 ± 3.5 |
| 7A7 | 79.8 ± 5.6 | 38.3 ± 6.4 |
| 7A13.1 | 95.7 ± 1.3 | 84.8 ± 0.4 |
| 7A14.1 | 90.4 ± 1.2 | 82.6 ± 1.6 |
| 7A15.1 | 85.8 ± 4.6 | 78.5 ± 6.9 |
| + Human Serum | 98.1 ± 0.5 | 95.4 ± 1.6 |
| − Human Serum | 17.7 ± 7.7 | 3.9 ± 0.9 |

*Calculated vs. PBS as negative control.

D. Ascites Production

Clones producing the antibodies listed in Tables 1 and 2 were grown to appropriate concentrations in tissue culture flasks and ascites fluid produced by injecting $1 \times 10^7$ cells of a given clone into BALB/c mice which were primed with 2,6,10,14-tetramethylpentadecane, available from Aldrich Chemical Company under the trade name Pristene. After two to three weeks, ascites was collected and centrifuged at 1000×g, 4° C. for 15 minutes to obtain ascitic supernatant. The monoclonal antibody in the ascites was characterized for immunoglobulin subclass, specificity of the monoclonal antibody in the ascites fluid was the same as that obtained from those generated in tissue culture. The data obtained from the competitive ELISA as described in C(i)(a) above of monoclonal antibodies produced in ascites fluid is shown in Table 4.

TABLE 4

| Ascites Fluid Dilution | % Competition* | | | | |
|---|---|---|---|---|---|
| | 7A6.4 | 7A7 | 7A13.1 | 7A14.1 | 7A15.1 |
| $1 \times 10^3$ | 97.0 | 92.3 | 96.5 | 86.8 | 85.3 |
| $5 \times 10^3$ | 88.4 | 64.5 | 85.0 | 48.2 | 45.7 |
| $1 \times 10^4$ | 76.9 | 54.6 | 63.8 | 29.6 | 34.3 |
| $5 \times 10^4$ | 25.7 | 14.0 | 16.6 | 14.5 | 8.4 |

*Calculated vs. non-specific ascites as negative control.

E. Purification of Monoclonal Antibody

The IgG monoclonal antibody was purified from the ascites fluid by protein-A chromatography. A column was packed with 10 mL Protein-A sepharose (Pharmacia Fine Chemicals) and equilibrated with 3.0 M sodium chloride, 1.0 M glycine, pH 8.8. Ten milliliters of ascites fluid was mixed with 10 mL of this buffer and loaded onto the column. The column was washed with this buffer until the absorbance of 280 nm returned to baseline. Monoclonal antibody was eluted with 0.1 M sodium citrate, pH 3.0 and 5 mL fractions were collected. The fractions containing protein, as determined by absorbance at 280 nm, were pooled, dialyzed into 10 mM sodium phosphate, 300 mM sodium chloride, pH 7.0, and filtered through 0.2 μm filters. The purified monoclonal antibody was concentrated to 6 times the original volume and assessed for its protein concentration, purity, and immunologic reactivity.

F. Conjugation of Purified Monoclonal Antibody

An enzyme-labeled conjugate was made by coupling the purified IgG monoclonal antibody to horseradish peroxidase. 10 mg of IgG was dissolved in 10 mM carbonate-bicarbonate buffer, pH 5.0 and dialyzed overnight at 4° C. against the same solution. 10 mg of enzyme grade horseradish peroxidase, HRP, (Boehringer Mannheim GMBH, W. Germany) was dissolved in 5 mL of distilled water, then mixed with 1 mL of a freshly prepared aqueous 0.2M sodium periodate solution and stirred for 20 minutes at room temperature. The solution was dialyzed overnight against 1 mM sodium acetate buffer, pH 4.5. After dialysis, the pH of the solution was adjusted to pH 9.5 and the 20 mg of IgG was immediately added. The pH was checked to ensure it was at a pH of 9.5 and the reaction mixture was stirred for 2 hours at room temperature. A fresh solution of sodium borohydride (50 mg/mL) was added to yield a final concentration of 0.25 mg/mL, whereupon the mixture was stirred for 2 hours at 4° C. The reaction mixture was subsequently dialyzed overnight at 4° C. against PBS, pH 7.5 for 4 hours. The conjugate was purified on a S-400 column (Pharmacia) with PBS, pH 7.5 as the eluting buffer at a flow rate of 3.6 mL/hour. The absorbance of all the fractions was read at 280 nm and 368 nm to determine which fractions contained protein and HRP, respectively. The fractions which had absorbance at both these wavelengths contained HRP-conjugated monoclonal antibody.

The fractions were assayed for immunologic activity by ELISA. A microtiter plate was coated with 200 μL containing 50 ng of rHBcAg protein diluted in PBS, pH 7.2. After overnight absorption at 4° C., the plates were blocked with 1% BSA-PBS for 1 hour at ambient temperature. The conjugate fractions were diluted 1:1,000 in 0.1% BSA-PBS and 100 μL of each fraction was added to the wells, followed by addition of 100 μL of normal human serum not reactive to HBcAg. After a 90-minute incubation at room temperature the plates were washed and 200 μL of OPD solution was added and allowed to react for 15 minutes at room temperature. The reaction was stopped by adding 50 μL of 1 N H$_2$SO$_4$ and the absorbance determined at 492 nm. Fractions that produced an absorbance >0.5 were pooled.

Three antibodies (7A6.4, 7A7 and 7A13.1) purified and labeled in this manner were diluted 1:1000 and tested in the competitive ELISA assay described in C(i)(a) for competition with serial dilutions of the five unlabeled monoclonal antibodies (7A6.4, 7A7, 7A13.1, 7A14.1 and 7A15.2) to determine whether the binding sites of the different antibodies are the same. Results are shown in Table 5.

TABLE 5

| Unlabeled Antibodies | | | Labeled Antibodies | | | | | |
|---|---|---|---|---|---|---|---|---|
| | | | HRP-7A6.4 O.D. = 1.581[a] | | HRP-7A7 O.D. = 0.502 | | HRP-7A13.1 O.D. = 1.576[a] | |
| Antibody (stock concentration) | Dilution Tested | μg/mL Tested | O.D. 410 nm | % C[b] | O.D. 410 nm | % C | O.D. 410 nm | % C |
| 7A6.4 | $10^{-2}$ | 9.1 | 0.214 | 86.5 | 0.002 | 99.6 | 0.410 | 73.9 |
| (0.9 mg/mL) | $10^{-3}$ | 0.91 | 0.614 | 61.2 | 0.030 | 94.0 | 0.564 | 64.2 |
| | $10^{-4}$ | 0.091 | 1.192 | 24.6 | 0.270 | 46.2 | 1.266 | 19.7 |
| 7A7 | $10^{-2}$ | 7.8 | 0.331 | 79.1 | 0.039 | 92.2 | 0.290 | 81.6 |
| (0.78 mg/mL) | $10^{-3}$ | 0.78 | 0.613 | 61.2 | 0.010 | 98 | 0.555 | 64.8 |
| | $10^{-4}$ | 0.078 | 0.888 | 43.8 | 0.210 | 58.2 | 1.503 | 4.6 |
| 7A13.1 | $10^{-2}$ | 7.5 | 0.338 | 78.6 | 0.003 | 99.4 | 0.226 | 85.6 |
| (0.75 mg/mL) | $10^{-3}$ | 0.75 | 0.349 | 77.9 | 0.010 | 98.0 | 0.438 | 72.2 |
| | $10^{-4}$ | 0.075 | 1.452 | 8.2 | 0.135 | 73.1 | 1.446 | 8.2 |
| 7A14.1 | $10^{-1}$ | 22 | 1.599 | 0 | 0.260 | 48.2 | 1.364 | 13.4 |
| (0.22 mg/mL) | $10^{-2}$ | 2.2 | 1.599 | 0 | 0.452 | 9.9 | 1.578 | 0 |
| | $10^{-3}$ | 0.22 | 1.515 | 0 | 0.575 | 0 | 1.579 | 0 |
| 7A15.2 | $10^{-2}$ | 1.3 | 0.680 | 56.9 | 0.020 | 96.0 | 0.890 | 43.5 |
| (0.13 mg/mL) | $10^{-3}$ | 0.13 | 1.373 | 13.2 | 0.281 | 44.0 | 1.372 | 12.9 |
| | $10^{-4}$ | 0.013 | 1.468 | 7.1 | 0.449 | 10.6 | 1.437 | 8.8 |
| human | $10^{-2}$ | 31.1 | 0.170 | 89.2 | 0.002 | 99.6 | 0.094 | 94.0 |
| anti-HBcAg | $10^{-3}$ | 3.11 | 1.069 | 32.4 | 0.217 | 56.8 | 1.013 | 35.7 |
| (3.11 mg/mL) | $10^{-4}$ | 0.31 | 1.545 | 2.3 | 0.368 | 26.7 | 1.127 | 28.5 |

[a]Optical density in the absence of competing antibody.
[b]% C = % competition.

These results indicate that all of the monoclonal antibodies except 7A/14.1 bind to the same epitope, and that epitope is therefore an immunodominant epitope. Since 7A/14.1 partially inhibits 7A7 and competes effectively with human polyclonal anti-HBcAg, 7A/14.1 can be suggested to bind to the immunodominant site, however, a closely adjacent or overlapping epitope.

G. Use Of the HRP-Monoclonal Antibody in a Diagnostic Assay

Monoclonal antibody 7A6.4 conjugated to horseradish peroxidase was used to develop a competitive ELISA for the detection of antibodies to HBcAg in human serum or plasma. Wells of a microtiter plate were coated with 200 μL of HBcAg diluted in PBS. pH 7.5, yielding a concentration of 50 ng/well. After overnight absorption, the wells were blocked with 250 μL of 1% bovine serum albumin in PBS for 1 hour at room temperature. The plates were washed three times with PBS and air dried.

Two hundred and six serum and plasma samples from a normal blood donor population were assayed with the HRP-monoclonal antibody assay. Equal volumes (100 μL) of horseradish peroxidase conjugated monoclonal antibody and human plasma or serum were added to the microtiter well and incubated for 90 minutes at room temperature. A positive control sample, known to be reactive to HBcAg, and a negative control sample were also assayed in duplicate. The wells were washed 6 times with PBS and blotted dry on absorbent paper. Two hundred microliters of OPD solution was added to each well and incubated for 30 minutes. The reaction was stopped by adding 50 μL of 1 N sulfuric acid to each well and the absorbance read at 492 nm.

The presence or absence of antibodies to HBcAg was determined by comparing the absorbance of the sample to a cut-off value. This cut-off was calculated from the mean of the negative and positive control absorbances using the following equation: 0.4 (negative control mean) +0.6 (positive control mean). Samples with an absorbance value equal to, or lower than, the cut-off value are considered reactive for antibodies to HBcAg. Those specimens with an absorbance value higher than the cut-off are considered negative. The cut-off value was calculated to be 0.467. Fifteen samples competed with the HRP-monoclonal antibody and were therefore reactive for antibodies to HBcAg. This assay was repeated using HRP-human anti-HBcAg and those same samples were also found to be reactive for antibodies to HBcAg. The results of this study are summarized in Table 6.

TABLE 6

| | PATIENT CORRELATION | |
|---|---|---|
| | Frequency | |
| Absorbance at 492 nm | HRP-Monoclonal Antibody | HRP-Human Polyclonal Antibody |
| 0.0–0.1 | 14 | 14 |
| 0.1–0.2 | 0 | 0 |
| 0.2–0.3 | 1 | 1 |
| 0.3–0.4 | 0 | 0 |
| 0.4–0.5 | 0 | 0 |
| 0.5–0.6 | 2 | 5 |
| 0.6–0.7 | 1 | 5 |
| 0.7–0.8 | 3 | 21 |
| 0.8–0.9 | 2 | 51 |
| 0.9–1.0 | 6 | 53 |
| >1.0 | 177 | 56 |

EXAMPLE 2

ALTERNATE DIAGNOSTIC ASSAY PROCEDURE

A. Antibody Production and Purification

Hybridoma cell line 7A6.4 was chosen for further assay development. This cell line was recloned by limiting dilution and subclone 7A6.4.3 was selected for production of ascites. This subclone was shown to react as expected in the assays described in Example 1.C. Ascites was produced as described in Example 1.D, and the monoclonal antibody purified as described in Example 1.E.

B. Antibody-HRP Conjugate Production and Purification

The purified monoclonal antibody was conjugated to HRP as described in Example 1.F, except that the conjugate was purified using a Zorbax ® Bioseries GF-450XL preparative HPLC column rather than using the S-400 column. The conjugate was eluted from the HPLC column with 0.15 M phosphate buffer, 0.01% thimerosal. pH 7.0. the conjugate elutes at approximately the void volume of the column as a broad peak free from any unreacted enzyme and antibody. The entire peak is pooled and diluted with 0.09 M tris(hydroxymethyl)aminomethane, 0.135 sodium chloride, 20% fetal calf serum, 0.01% thimerosal, pH 7.5 (stabilizing buffer) so that the absorbance at 280 nm is approximately 0.025. The conjugate is further diluted in stabilizing buffer before use. The final dilution is determined using the ELISA procedure described in Example 1.F.

C. Diagnostic Assay Procedure

The microtiter plates were coated with rHBcAg as described in Example 1.G. 100 μL of sample was added to a designated well of the plate. Within 30 minutes 100 μL of the conjugate prepared in B above was added, the plate was covered and incubated for approximately 1 hour at approximately 37° C.. The plate was then washed 6 times with PBS containing Tween 20 surfactant and chloracetamide as preservative. Any drops of wash buffer remaining were removed by firmly striking the plate twice on an absorbant surface. 100 μL of a substrate solution containing 25 mM OPD, 25 mM citrate and 0.03% hydrogen peroxide was then added to each well of the plate and the plate incubated for approximately 30 minutes in the dark. The enzyme reaction was stopped by addition of 100 μL of 1 N $H_2SO_4$ and the absorbance at 492 nm was measured. A negative control consisting of recalcified human plasma nonreactive for Hepatitis B Surface antigen (HBsAg), anti-HBsAg and anti-HBcAg was tested in triplicate. A positive control consisting of recalcified human plasma which is reactive for anti-HBcAg was tested in duplicate. The cutoff value was calculated by multiplying the average of the negative control responses by 0.25. Values less than the cutoff are considered reactive for anti-HBcAg, those greater than the cutoff are considered nonreactive. Two known reactive plasma samples and six known nonreactive plasma samples were tested according to this procedure. A representative data set is reported in Table 7.

TABLE 7

| Sample # | Absorbance (492 nm) | Result (+/−) |
|---|---|---|
| Pos. Control | 0.180 (Avg. of Two) | — |
| Neg. Control | 1.421 (Avg. of Three) | — |
| 1 | 0.184 | + |
| 2 | 2.038 | − |
| 3 | 0.638 | − |
| 4 | 2.759 | − |
| 5 | 1.688 | − |
| 6 | 0.602 | − |
| 7 | 0.147 | + |
| 8 | 2.482 | − |

What is claimed is:

1. In a single-antibody inhibition assay for detecting antibody to hepatitis B core antigen (HBcAg) in a patient sample comprising:
   (1) incubating the sample and labeled antibody to HBcAg with HBcAg bound to a solid support;
   (2) washing the support to remove unbound labeled antibody; and
   (3) detecting antibody to HBcAg in the patient sample by measuring the signal generated by labeled antibody bound to the HBcAg or not bound to the HBcAg; the improvement which comprises using as the labeled antibody a monoclonal antibody which is specific for an immunodominant site on HBcAg.

2. Assay of claim 1 wherein the label is an enzyme.

3. Assay of claim 2 wherein the sample and labeled antibody are incubated with the HBcAg simultaneously.

4. Assay of claim 3 wherein the antibody is an antibody produced by a cell line on deposit with ATCC and having the accession number HB-9265, HB-9262, HB-9264, HB-9263, or HB-9261.

5. Assay of claim 4 wherein the antibody is an antibody produced by the cell line having accession number HB-9265.

6. Assay of claim 2 wherein the sample is incubated with the HBcAg before addition of labeled antibody.

7. Assay of claim 6 wherein the antibody is an antibody produced by a cell line on deposit with ATCC and having the accession number HB-9265, HB-9262, HB-9264, HB-9263, or HB-9261.

8. Assay of claim 7 wherein the antibody is produced by the cell line having accession number HB-9265.

9. Assay of claim 1 wherein the label is associated with the antibody through binding of another substance which is itself detectably labeled.

10. Assay of claim 9 wherein the label is an enzyme.

11. A reagent kit for conducting an assay for antibody to hepatitis B core antigen (HBcAg) comprising, in one or more containers HBcAg bound to a solid support and a labeled monoclonal antibody which is specific for an immunodominant site on HBcAg.

12. Kit of claim 11 wherein the label is an enzyme and the antibody is an antibody produced by a cell line on deposit with ATCC and having the accession number HB-9265, HB-9262, HB-9264, HB-9263, or HB-9261.

13. Kit of claim 12 wherein the label is horseradish peroxidase or alkaline phosphatase and the antibody is produced by the cell line having the accession number HB-9265.

14. A competitive enzyme-linked immunosorbent assay (ELISA) method of screening hybridoma supernatants for monoclonal antibodies to hepatitis B core antigen (HBcAg) which comprises:
   (1) incubating supernatant samples and enzyme-labeled human anti-HBcAg polyclonal antibodies with HBcAg bound to a support;
   (2) washing the support to remove unbound labeled antibody; and
   (3) adding a solution of enzyme substrate and measuring the absorbance of the mixture to indicate presence of monoclonal antibodies to HBcAg.

15. A competitive enzyme-linked immunosorbent assay (ELISA) method of screening hybridoma supernatants for monoclonal antibodies to immunodominant epitopes of multiple epitope antigens which comprises:
   (1) incubating supernatant samples and labeled polyclonal antibodies to the antigen with antigen bound to a support;
   (2) washing the support to remove unbound labeled antibodies; and
   (3) detecting the bound labeled antibodies wherein monoclonal antibodies which inhibit binding of the labeled polyclonal antibodies to antigen bound to the support by more than about 40% are immunodominant.

16. A method of producing monoclonal antibody to rHBcAg which comprises immunizing a mouse with intraperitoneal and intravenous injections of rHBcAg totalling less than 100 μg over a period less than 3 weeks, fusing spleen cells from the immunized mouse with mouse myeloma cells, culturing the fused cells in selective medium to produce a continuous hybrid cell line and cloning the cells to produce the antibody.

17. Hybrid cell lines on deposit with ATCC and having accession numbers HB-9265, HB-9262, HB-9264, HB-9263, and HB-9261.

18. Monoclonal antibodies to HBcAg produced by the cell lines of claim 17.

* * * * *